(12) United States Patent
McTavish et al.

(10) Patent No.: US 10,744,084 B2
(45) Date of Patent: Aug. 18, 2020

(54) NON-SPECIFIC DELAYED-TYPE HYPERSENSITIVITY RESPONSE TO TREAT HERPES SIMPLEX VIRUS INFECTION

(71) Applicants: Squarex, LLC, Pine Springs, MN (US); Bioventures, LLC, Little Rock, AR (US)

(72) Inventors: Hugh McTavish, Pine Springs, MN (US); Thomas Dag Horn, Boston, MA (US); Sandra Marchese Johnson, Greenwood, AR (US)

(73) Assignees: Squarex, LLC, Pine Springs, MN (US); Bioventures, LLC, Little Rock, AR (US)

( * ) Notice: Subject to any disclaimer, the term of this patent is extended or adjusted under 35 U.S.C. 154(b) by 0 days.

(21) Appl. No.: 16/186,113

(22) Filed: Nov. 9, 2018

(65) Prior Publication Data
US 2019/0105263 A1    Apr. 11, 2019

Related U.S. Application Data

(63) Continuation of application No. 14/960,402, filed on Dec. 6, 2015, which is a continuation of application No. 14/690,459, filed on Apr. 19, 2015, now Pat. No. 9,205,065, which is a continuation of application No. 12/450,586, filed as application No. PCT/US2008/004392 on Apr. 4, 2008, now abandoned.

(60) Provisional application No. 60/921,806, filed on Apr. 4, 2007.

(51) Int. Cl.
| | |
|---|---|
| *A61K 31/12* | (2006.01) |
| *A61K 9/00* | (2006.01) |
| *A61K 31/08* | (2006.01) |
| *A61K 31/13* | (2006.01) |
| *A61K 31/04* | (2006.01) |
| *A61K 31/122* | (2006.01) |
| *A61K 31/047* | (2006.01) |
| *A61K 31/4745* | (2006.01) |
| *A61K 39/00* | (2006.01) |
| *A61K 39/165* | (2006.01) |
| *C12N 7/00* | (2006.01) |

(52) U.S. Cl.
CPC ............ *A61K 9/0019* (2013.01); *A61K 31/04* (2013.01); *A61K 31/047* (2013.01); *A61K 31/08* (2013.01); *A61K 31/122* (2013.01); *A61K 31/13* (2013.01); *A61K 31/4745* (2013.01); *A61K 39/0002* (2013.01); *A61K 39/165* (2013.01); *C12N 7/00* (2013.01); *A61K 2039/54* (2013.01); *A61K 2039/545* (2013.01); *A61K 2039/58* (2013.01); *C12N 2760/18733* (2013.01)

(58) Field of Classification Search
CPC ..................................................... A61K 31/122
USPC .......................................... 514/690; 424/400
See application file for complete search history.

(56) References Cited

U.S. PATENT DOCUMENTS

| | | | |
|---|---|---|---|
| 4,214,592 A | 7/1980 | Jacquet | |
| 5,846,559 A | 12/1998 | Hoppe | |
| 5,965,354 A | 10/1999 | Burke | |
| 6,292,752 B1 | 9/2001 | Franke et al. | |
| 6,350,451 B1 | 2/2002 | Horn | |
| 6,355,251 B1 * | 3/2002 | Zamoyski | A61K 8/4973 424/195.15 |
| 6,375,952 B1 | 4/2002 | Koelle | |
| 6,562,802 B2 | 5/2003 | Johnson | |
| 6,761,900 B2 | 7/2004 | Shudo | |
| 7,037,509 B2 | 5/2006 | Koelle | |
| 2002/0142005 A1 | 10/2002 | Horn | |
| 2004/0076646 A1 | 4/2004 | Caplan | |

FOREIGN PATENT DOCUMENTS

| | | |
|---|---|---|
| WO | WO 2003/37067 | 6/2000 |
| WO | WO 02/070281 | 9/2002 |

OTHER PUBLICATIONS

Manome et al. "Simple chemicals can induce maturation and apoptosis of dendritic cells," Immunology 1998, vol. 98, pp. 481-490 (Year: 1998).*
Silverberg et al. "Squaric acid immunotherapy for warts in children," J. Am. Acad. Dermatol. 2000, vol. 42, No. 5, Part 1, pp. 803-808 (Year: 2000).*
Eriksen "Treatment of the common wart by induced allergic inflammation." Dermatologica, 1980, vol. 160, No. 3, pp. 161-166, Medline Abstract, PubMed ID 7389963 (Year: 1980).*
Eriksen "Treatment of the common wart by induced allergic inflammation." Dermatologica, 1980, vol. 160, No. 3, pp. 161-166, Google Scholar search report (DMSO+WART) (Year: 1980).*
International Preliminary Report on Patentability of parent international application PCT/US2008/004392, from which the present application claims priority (as a continuation of U.S. Appl. No. 12/450,586, which is a national stage of PCT/US2008/004392).
Buckley, D.A. et al. 2001, The therapeutic use of topical contact sensitizers in benign dermatoses. *Br. J. Dermatology* 145:385-405.
Kurokowa et al. The Journal of Pharmacology and Experimental Therapeutics, 1999, vol. 289, No. 1, p. 72-78.
Lee et al. Journal of the American Academy of Dermatology, 1999, vol. 41, pp. 595-599.
Roberts et al. 1993. Clinical Psychology Review 13:375-391.
Cardinali et al. 2004. Acta Derm. Vereol. 84:223-226.
Jarisch et al. 1977. Arch Derm Res. 258:151-159.
Palli, M. A., H. McTavish, A. Kimball, and T. D. Horn. 2017. Immunotherapy of Recurrent Herpes Labialis With Squaric Acid. *JAMA Dermatol.* 153:828-829.

(Continued)

*Primary Examiner* — Shengjun Wang
(74) *Attorney, Agent, or Firm* — Hugh McTavish

(57) ABSTRACT

A method is presented for treating herpes simplex virus (HSV) infection comprising: (a) locally administering a substance that induces a delayed type hypersensitivity (DTH) response to a patient at a site of an HSV lesion to induce a DTH response at the site of the lesion during one or more outbreaks of the HSV infection.

8 Claims, No Drawings

(56) References Cited

OTHER PUBLICATIONS

McTavish H, Zerebiec KW, Zeller JC, Shekels LL, Matson MA, Kren BT. 2019. Immune characteristics correlating with HSV-1 immune control and effect of squaric acid dibutyl ester on immune characteristics of subjects with frequent herpes labialis episodes. *Immun. Inflamm. Dis.* 7(1):22-40.

Morison, WL. Anti-viral treatment of warts. *British J. Dermatol.* 1975, vol. 92, pp. 97-99.

Eriksen, K. 1980. Treatment of the common wart by induced allergic inflammation. *Dermatologica* 160:161-166.

*Recurrent Herpes Labialis: Developing Drugs for Treatment and Prevention Guidance for Industry.* Nov. 2017. U.S. Department of Health and Human Services, Food and Drug Administration, Center for Drug Evaluation and Research (CDER).

\* cited by examiner

NON-SPECIFIC DELAYED-TYPE HYPERSENSITIVITY RESPONSE TO TREAT HERPES SIMPLEX VIRUS INFECTION

BACKGROUND

Herpes simplex virus (HSV) causes painful lesions on the skin or mucous membranes characterized by vesicles filled with a clear fluid. HSV type 1 (HSV-1) commonly infects the mouth, face, and eyes. HSV type 2 commonly infects the genitals and buttocks. But each serotype can cause infection in all these locations. (Stalkup J R et al., Chapter 80, Human Herpesviruses in *Dermatology*, Bolognia J L et al. eds. 2003, Mosby Edingurgh, United Kingdom).

Primary infection with HSV typically causes mild fever and lesions at the site of infection. Healing occurs in 8-12 days on average, whereupon the virus migrates to nerve ganglia, where it resides in a latent phase. The virus can be activated again by multiple causes, including physical or emotional stress, colds, fever, immune suppression, or no apparent cause. Activation results in secondary outbreaks. For HSV-1, this usually involves cold sores on the vermillion border of the lips. For HSV-2, the secondary outbreak most commonly causes lesions in or around the genitals, including the vulva, vagina, or penis.

Itching, tingling, and a burning sensation usually precede localized erythema of the skin or mucous membranes by a few hours. Vesicles then form on the skin or mucous membranes. After a few days the ulcers dry and become crusted and generally heal in about 10 days.

The outbreaks cause local pain and a mild generalized fever in many cases.

HSV-2 is generally transmitted by sexual contact. HSV-1 is thought to be transmitted by contact with saliva containing the virus. Infection with one or both serotypes of HSV is extremely common. Some have estimated that 90% of the world's population have antibodies to HSV-1. Forty to sixty million persons in the U.S. are infected with HSV-2. (Stalkup J R et al., Supra.)

There is no cure for HSV infection. Antiviral therapy marginally reduces viral shedding and symptoms in secondary outbreaks. Antiviral therapeutics can heal chronic infection in immunocompromised patients. Antiviral therapeutics are also used prophylactically. But antivirals do not cure the infection, and prophylactic antiviral therapy therefore may be needed for a patient's entire life. (Chakrabarty A et al. 2005, *Skin Therapy Lett.* 10(1):1-4.) Even with prophylactic use of antivirals, outbreaks still typically occur, although at a lower frequency. Commonly used antivirals for HSV include acyclovir and its derivatives, e.g., valacyclovir and famciclovir. They are usually given orally, but can also be administered by i.v. or in a topical cream. Docosanol cream (ABREVA) has also been shown to decrease the duration of outbreaks slightly (Sacks S L et al. 2001, *J Am Acad Dermatol.* 45(2):222-30).

New substances and methods to treat HSV infection are needed.

SUMMARY

The invention involves administering a substance that induces a delayed-type hypersensitivity (DTH) reaction locally at a site of an HSV lesion during an outbreak. This causes T cells to swarm the area of the lesion, which has a high concentration of virus. This appears to train the immune system to recognize the herpes simplex virus and strengthens the immune response to the virus, which lessens the severity and frequency of subsequent HSV outbreaks (e.g., cold sores or genital outbreaks) after the treated outbreak or outbreaks. Any compound or mixture that induces a DTH response can be used, including squaric acid dibutyl ester (SADBE), diphenylcyclopropenone (DPCP), 1-chloro-2,4-dinitrobenzene (DNCB), and extract of poison ivy leaves. Protein antigens that induce a DTH response, such as mumps antigen or other antigens a patient might have immunity against, can also be injected into the skin or mucous membrane at the site of an outbreak. The invention has been tested with cold sores, which are caused by herpes simplex virus type 1. It also works with genital herpes, caused by herpes simplex virus type 2.

One embodiment of the invention involves a method of treating herpes simplex virus (HSV) infection comprising: locally administering a substance that induces a delayed type hypersensitivity (DTH) response to a patient at a site of an HSV lesion to induce a DTH response at the site of the lesion during one or more outbreaks of the HSV infection.

Another embodiment of the invention provides a medical use of a substance capable of inducing a delayed-type hypersensitivity response in humans to prepare a medicament effective to reduce the frequency or severity of subsequent HSV outbreaks in a patient with HSV infection.

DETAILED DESCRIPTION

One embodiment of the invention involves a method of treating herpes simplex virus (HSV) infection comprising: locally administering a substance that induces a delayed type hypersensitivity (DTH) response to a patient at a site of an HSV lesion to induce a DTH response at the site of the lesion during one or more outbreaks of the HSV infection. An "outbreak" refers to a temporal episode of burning, tingling, painful, or visible lesions arising from HSV infection. Outbreaks are separated by dormant periods when the patient has no symptoms of infection.

A delayed-type hypersensitivity (DTH) response, also known as a type IV hypersensitivity response, is an immune response that typically reaches maximal intensity 24-48 hours after contact with an immunogen. It produces visible erythema at the site of contact with the immunogen. A DTH response is primarily a T cell response (Goldsby, Richard A. et al. 2000, *Kuby Immunology*, 4th edition, WH Freeman and Co., New York, chapter 16). It occurs when antigen activates sensitized $T_{DTH}$ cells. Activation of the $T_{DTH}$ cells results in secretion of several cytokines, which draws macrophages into the area and activates them.

T cells and cell-mediated immunity are the primary arm of the immune system responsible for fighting viral infection. Cell-mediated immunity is responsible for recognizing and eliminating cells that harbor intracellular pathogens, such as HSV. Without wishing to be bound by theory, the inventors believe the DTH response of the present invention causes T cells to swarm the area of an HSV outbreak. With a large number of HSV viral particles and HSV proteins in the area during an outbreak, the T cells better learn to recognize HSV and cells harboring HSV, resulting in a stronger immune response to HSV in the future that does a better job of ridding the body of the virus and viral-infected cells, thus preventing outbreaks and lessening the severity of outbreaks. This is a process of "epitope unveiling" whereby epitopes that were poorly recognized by the immune system become better recognized.

It has previously been shown that warts caused by human papilloma virus can be treated by inducing a DTH response at the site of a wart with topical application of contact sensitizers, such as DNCB, or with intralesional injection of protein antigens unrelated to human papilloma virus that induce a DTH response in the patient, such as mumps antigen, candida antigen, or trichophyton antigen. (U.S. Pat. No. 6,350,451; U.S. published patent application no. 20050175634; Johansson, E. et al. 1984, Dinitrochlorobenzene (DNCB) treatment of viral warts, *Acta Derm. Verereol (Stockh)* 64:529-533; Dunnigan, W. G. et al., 1982, Dinitrochlorobenzene immunotherapy for verrucae resistant to standard treatment modalities, *J. Am. Acad. Dermatol.* 6:40-45.) The present invention appears to work by a similar mechanism.

The immunogen of the present invention used to induce the DTH response can be a protein antigen that the subject has previously encountered and to which he or she has developed immune recognition. This is the principle of skin tests for allergens or antigens such as the tuberculosis antigen. The immunogen can also be a topical sensitizer, such as urushiol, an oil that is the active irritating ingredient in poison ivy, poison oak, and other irritating plants. Topical sensitizers are typically haptens. Haptens are small molecules that do not induce an immune response on their own, but can induce an immune response and antibodies that specifically recognize the hapten determinant when attached to proteins or other macromolecules. Topical sensitizers are typically haptens that react with proteins in the skin to form adducts that are immunogenic.

Thus, in some embodiments the substance that induces a DTH response is a topical contact sensitizer—a substance that when applied topically to human skin induces a DTH response.

Thus, in some embodiments the method involves topically applying a substance that induces a DTH response to a patient at a site of an HSV lesion to induce a DTH response at the site of the lesion.

A topically applied contact sensitizer is typically applied as a solution in an organic solvent, e.g., acetone or dimethylsulfoxide. If soluble in water, it can instead by applied in an aqueous solution. It can also be applied in a cream, ointment, lotion, oil, etc.

In specific embodiments where the substance that induces a DTH response is applied topically (is a topical contact sensitizer) the substance is squaric acid dibutyl ester (SADBE), diphenylcyclopropenone (DPCP), 1-chloro-2,4-dinitrobenzene (DNCB), or 1-chloro-2,6-dinitrobenzene. In some embodiments, the substance is squaric acid or an ester thereof.

The structure of squaric acid is shown below.

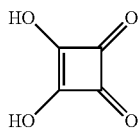

These contact sensitizers are available from several commercial sources, including Spectrum Chemicals & Laboratory Products, a division of Spectrum Chemical Manufacturing Corp., Gardena, Calif. and New Brunswick, N.J.

In other embodiments, the substance that induces a DTH response comprises urushiol or an extract of an irritating plant.

In other embodiments, the substance that induces a DTH response is a protein antigen. The protein antigen is typically not an HSV antigen, although it could be. Any antigen that induces a DTH response can be used. A subject may have a preexisting sensitivity to the antigen. Mumps antigen, candida antigen, and trichophyton antigen are three preferred antigens in this regard, since a large percentage of the population has a preexisting sensitivity to one or more of these antigens. Any foreign (non-self) antigen to which a subject does not have a preexisting sensitivity can also be used. In that case, the subject should be sensitized to the antigen by administering the antigen to the subject (i.e., immunizing the subject with the antigen) before locally administering the antigen to the subject at a site of HSV outbreak to induce a DTH response at the site of an outbreak.

Thus, in some embodiments, the method involves intralesionally (e.g., intradermally) injecting the substance that induces a DTH response into a patient at a site of an HSV lesion in the patient to induce a DTH response at the site of the lesion.

In a specific embodiment of intralesionally injecting the substance, the substance comprises mumps antigen, candida antigen, or trichophyton antigen.

The dosages of antigen can be approximately the same as the dosages used in skin tests with these antigens. The dose should be a dose that induces a mild to moderate DTH response.

In a specific embodiment, the method further comprises before inducing a DTH response at the site of an outbreak, administering the substance that induces a DTH response to the patient to develop a sensitivity to the substance in the patient. This presensitization step can be done with intralesionally injected antigens or with topically applied substances. For the presensitization step, the substance can be administered at the site of outbreak. This may be beneficial to help stimulate recognition of HSV and HSV-infected cells. Or for the presensitization step, the substance can be administered anywhere. For instance, a topical contact sensitizer may be administered on the forearm, or an injectable antigen may be administered by intradermal injection to the forearm, during a time when the patient may or may not be suffering an outbreak.

In a specific embodiment, the method can involve, before the step of inducing a DTH response at the site of an HSV lesion, administering the substance that induces a DTH response to the patient at at least one dosage level to determine a dosage level of the substance to administer to induce a DTH response at the site of an HSV lesion.

The lips and genitals, which are the most common areas for lesions of HSV-1 and HSV-2 outbreaks respectively, are both very sensitive areas. The lips are also a very visible area. Thus, it is desirable to not induce a severe DTH response in these sites because such a severe response can be painful and unsightly. Therefore, one may want to test one or more dosages of the substance in a less sensitive and less visible area, such as the forearm, to find a dose that induces an appropriate level of DTH response before applying the substance at the site of an HSV lesion. It has been found that the method works even when the DTH response at the site of an HSV lesion is fairly mild. It does not appear to be necessary to induce a severe DTH response. But the methods may be more effective in inducing a sustained immunity to HSV that prevents subsequent outbreaks if the DTH response is stronger.

For DNCB, a suitable sensitizing dose appears to be a 2% DNCB solution in acetone, dimethylsulfoxide (DMSO), or another solvent, and a suitable treatment dose is, for example, 0.05 to 2.0% DNCB. A suitable sensitizing dose of SADBE is a 2% solution, and a suitable treatment dose is, for example, a 0.05%-2% solution. Doses that are higher or lower than these ranges can also be used in some patients.

The topical contact sensitizer solution in one embodiment is applied by dabbing a cotton-tipped swab that has been saturated with the solution onto the skin or mucous membrane at the desired site of application, without repeated rubbing or spreading the solution over an extended area. For both the sensitization and treatment applications, the topical contact sensitizer is preferably left on the skin for at least a few hours before washing it off.

In another embodiment, the contact sensitizer solution is applied with a fixed volume device, such as a micropipette, syringe, or microsyringe. This allows application of a defined volume and therefore a defined amount of the contact sensitizer. That can be helpful to produce a more predictable level of intensity of the DTH response. A typical volume is 2-40 microliters to be able to apply the solution to a targeted and limited area such as a lesion without the solution spreading or running to nontarget areas.

In particular embodiments of the methods, the herpes simplex virus is HSV type 1. In other embodiments, it is HSV type 2.

In particular embodiments, the method involves administering the substance that induces a DTH response at the site of an HSV lesion on or adjacent to the lip of the patient.

In particular embodiments, the method involves administering the substance that induces a DTH response at the site of an HSV lesion on the genitals of the patient.

In particular embodiments, the method involves topically applying the substance that induces a DTH response to skin at a site of an HSV lesion. In other embodiments, it involves topically applying the substance to a mucous membrane at a site of an HSV lesion.

The method can reduce the severity of future outbreaks or the frequency of future outbreaks, or both. The method is not intended to reduce the severity of the outbreak during which the DTH response is elicited at the site of an HSV lesion. In fact, it may actually worsen that particular outbreak. The DTH response involves inflammation and can produce a mild fever. Inflammation and fever are themselves triggers for HSV outbreaks, so the DTH response may trigger the HSV to worsen its current outbreak. But once that outbreak subsides or is brought under control, subsequent outbreaks are found to be much less frequent and/or severe.

To counteract the tendency of the DTH response to worsen the HSV outbreak during which the DTH response is induced, in one embodiment, the method can involve treating the patient with antiviral medications, such as acyclovir or valacyclovir, during the outbreak in which the DTH response is induced.

The step of inducing a DTH response at a site of an HSV lesion can be repeated more than once to further strengthen the immune response to HSV, if further outbreaks occur. Preferably, treatments are spaced apart by at least two weeks to allow full development of the immune response from the previous treatment.

Many patients may require more than one treatment to develop a level of immunity that decreases the number or severity of subsequent outbreaks (i.e., outbreaks subsequent to the treatment, outbreaks in which no substance is administered to induce a DTH response). Preferably, the immunity developed completely prevents subsequent outbreaks. Thus, the substance that induces a DTH response is administered to a lesion in one outbreak. When the outbreak subsides and a subsequent recurrent outbreak occurs, the substance may be administered to a lesion again. After administration of the substance during 1 to 3 or more outbreaks, the patient may have no outbreaks for an extended period of time. But the immunity may eventually wear off, and outbreaks may recur. A substance that induces the DTH response can then be applied again during one or more outbreaks as needed to develop immunity again that prevents outbreaks.

Thus, in one embodiment the method comprises: (a) locally administering a substance that induces a delayed type hypersensitivity (DTH) response to a patient at a site of an HSV lesion to induce a DTH response at the site of the lesion during one outbreak of the HSV infection (for example, during only one outbreak over a 6-month period). In one embodiment the method comprises: locally administering a substance that induces a delayed type hypersensitivity (DTH) response to a patient at a site of an HSV lesion to induce a DTH response at the site of the lesion during one outbreak of the HSV infection; wherein the method does not comprise administering a substance that induces a DTH response to the patient at a site of an HSV lesion to induce a DTH response at the site of the lesion during another outbreak within 3 months before or after the one outbreak.

The method of claim 1 wherein the method comprises: (a) locally administering a substance that induces a delayed type hypersensitivity (DTH) response to a patient at a site of an HSV lesion to induce a DTH response at the site of the lesion during two or more outbreaks of the HSV infection (for example, during two or more outbreaks in a 6-month period).

One embodiment of the invention provides a medical use of a substance capable of inducing a delayed-type hypersensitivity response in humans to prepare a medicament effective to reduce the frequency or severity of herpes simplex virus (HSV) outbreaks.

In particular embodiments, the substance is a topical contact sensitizer capable of inducing a DTH response in humans when administered topically.

In other embodiments, the substance is an antigen capable of inducing a DTH response in humans when injected intradermally.

By reducing the duration and severity of subsequent outbreaks, the methods of the invention also reduce transmission of infection. This is true for both HSV-1 infection and HSV-2 infection, and of both genital herpes and oral herpes.

In one embodiment of the methods, the method reduces transmission of infection of HSV-1.

In one embodiment of the methods, the method reduces transmission of infection of HSV-2.

In one embodiment of the methods of the invention, the method reduces transmission of oral herpes infection.

In one embodiment of the methods of the invention, the method reduces transmission of genital herpes infection.

In specific embodiments, the methods decrease frequency of subsequent outbreaks by at least 50% (i.e., increase time to next outbreak after treatment by at least 100%). In other embodiments, the methods decrease frequency of subsequent outbreaks by at least 75%. In other embodiments, the methods decrease frequency of subsequent outbreaks by at least 70%, at least 80%, or at least 90%. In one embodiment, the methods increase time between outbreaks. In specific embodiments, the methods increase time between outbreaks (e.g., increase the time from resolution of the outbreak treated to the next subsequent outbreak, as compared to the average time between outbreaks previously) at least 2-fold, at least 3-fold, at least 4-fold, or at least 5-fold.

In specific embodiments, the methods of the invention reduce the duration of subsequent outbreaks. In particular embodiments, they reduce the time to healing of lesions in subsequent outbreaks by at least 10%, at least 20%, at least 30%, or at least 40%.

The methods are believed to stimulate cell-mediated immunity. Cell-mediated immunity may be assayed by peripheral blood mononuclear cell proliferation assays, as described in Example 2 below. In specific embodiments of the methods, the method increases stimulation index of peripheral blood mononuclear cells (as illustrated in Example 2) in a proliferation assay of stimulation by HSV particles. In specific embodiments, it increases the stimulation index from less than 30 before treatment to more than 30, more than 50, or more than 60 after treatment. In other embodiments, it increases the stimulation index from less than 50 before treatment to more than 50 or more than 60 after treatment. In other embodiments, it increases the stimulation index by at least 10, at least 20, at least 30, at least 40, or at least 50. In other embodiments, it at least doubles, at least triples, or at least quadruples the stimulation index.

Immune response enhancers can also be used with the substance that induces a DTH response to enhance development of immunity against HSV with the DTH response. One type of enhancer that can be used is a cytokine. Among the cytokines that may be used are an interferon (e.g., interferon alpha), granulocyte monocyte colony stimulating factor (GM-CSF), interleukin-2, and interleukin-12. Each of these has been shown to promote cell-mediated immune reactions or antiviral immune reactions (Kiline M O et al. 2006, *J. Immunol.* 177:6962-73; Arora A. et al 2006, *J. Surg. Oncol.* 94:403-412; Horn et al., US Published Patent Appl. No. 20050175634).

U.S. Published Patent Appl. 20050175634 reports intralesional injection of unrelated antigens to induce a DTH response in warts. It reports a study where a portion of the patients received intralesional injection of antigens only, and others received as well intralesional injection of interferon alpha or GM-CSF. A larger fraction of patients receiving interferon or GM-CSF together with the antigens responded to treatment than patients receiving antigen alone, although the number of subjects treated was not enough for the differences to be statistically significant.

Appropriate doses of the cytokines are known in the art or can be determined by experimentation to identify a dosage range that gives best results. A suitable dose of interferon alpha, for example, is approximately 1 million IU administered locally.

Administration of the cytokines may be by intadermal injection at the site of the lesion. It may also be by topical administration, e.g., in an ointment, cream, or lotion (Syed T A et al. 1995. *J. Mol. Medicine* 73:141-144).

In another embodiment, the immune response enhancer is a pharmaceutical agent that stimulates synthesis of cytokines. In one embodiment, it is a synthetic (i.e., not a naturally occurring molecule) pharmaceutical agent that stimulates synthesis of cytokines. Specific examples are imiquimod and resiquimod. (Spruance S L et al. 2001, *J. Infect. Dis.* 184:196-200; Bernstein D I et al. 2005, *Clinical Infectious Disease* 41:808-814.)

The immune response enhancer can be administered at any suitable time that will result in it having an effect during the DTH response. This may be at the same time as the time that the substance that elicits a DTH response is administered or somewhat before or after. It should be administered before or during the DTH response.

The invention will now be illustrated by the following examples. The examples are intended to illustrate the invention but not limit its scope.

EXAMPLES

Example 1

Treatment of an Individual Suffering from Frequent and Severe Cold Sores

The individual treated was one of the inventors. He is a male and was 42 years old at the time of this treatment. The subject suffered from frequent cold sores on the lower lip. The outbreaks typically lasted 7-10 days and frequently longer. The subject had suffered from frequent cold sores most of his life. During the 6 months prior to this treatment, the outbreaks had been almost continuous. After getting over one outbreak, the next outbreak would begin often within a week.

The subject was presensitized to DNCB by dipping a cotton-tipped swab in a 2% DNCB solution in acetone, and contacting the cotton-tipped swab with two spots on the forearm. No rash developed. Two weeks later, the subject again applied a 2% DNCB solution to his forearm at two small spots different from where the sensitizing dose had been applied. A very strong but localized rash ensued and lasted for 3 weeks. The subject then applied a 0.1%, 0.2%, and 0.3% solutions to separate small spots on the forearm. The 0.1% solution produced almost no erythema. The 0.2% solution produced a mild but easily seen erythema that began 2 days after applying the solution and lasted about 3 days. Based on this result, the 0.2% solution was chosen as the dosage to apply to the next cold sore.

Upon the next HSV outbreak that produced a cold sore on the subject's lower lip, the subject applied a 0.2% DNCB solution in acetone to the site of the cold sore on his lower lip and left it on overnight. In the morning he washed it off. A mild erythema in the area of the cold sore developed over 2-3 days and lasted a further 5 days, and the cold sore resolved in about 7 days, which was a typical duration for this individual or a slightly shorter duration than normal. Following this treatment, the subject experienced outbreaks of cold sores on his lower lip approximately weekly for the next 4 weeks, but they were much less severe and of much shorter duration than before. Each outbreak would begin and completely resolve in one day. Approximately two months after the first application of DNCB to his lip, the subject had a mild cold sore and applied the 0.2% DNCB solution in acetone to the site of an HSV lesion on his lower lip as soon as the outbreak began. This time, the inflammation and erythema with the application were more severe than they had been with the first application of DNCB to the lesion on his lip two months previously. We think this may be because the immune system was recognizing not just the DNCB but also the herpes virus antigens with this second application. With the greater inflammation, the cold sore outbreak was worse than any of the outbreaks between the first and second DNCB treatments. Those outbreaks had been very mild, but this HSV outbreak lasted for about 7 days, and was as severe or even slightly more severe than a typical outbreak before the DNCB treatments were undertaken. The outbreak seemed to worsen as the inflammation associated with the DTH response worsened, and only lessened when the DTH response subsided.

Following that second DNCB treatment at the site of a lesion, the subject had no outbreaks at all for 6 months, which he reports as the longest he has ever gone without a cold sore. At the end of this 6-month period, he had a mild cold sore and chose to apply a 0.1% DNCB solution to the cold sore. Again, this induced a moderate DTH response, and the inflammation seemed to worsen the outbreak, so the outbreak lasted about 10 days. When the outbreak subsided, the subject went another 6 months without any outbreaks to the present time.

For several months before and for the entire time described herein after the initial DNCB treatment, the subject took no antiviral medicines.

Example 2

Treatment of Herpes Labialis by Squaric Acid Dibutyl Ester

Thirty patients are recruited meeting the following criteria:

| Inclusion Criteria | Exclusion Criteria |
|---|---|
| 18-85 years old | |
| Men and non-pregnant/non-lactating women | Pregnancy or attempting to become pregnant |
| Able to understand and comply with all requirements of protocol | Unable to return for follow-up visits or comply with protocol |
| Six or more episodes of herpes labialis of a recurring nature per year | Prior treatment with Squaric Acid and current active therapy |
| | Cancer treatment and any immunodeficiency |

In a screening interview, vital signs are recorded, and information is collected on any medications the patient is currently taking, previous and current treatments for cold sores, severity and duration of cold sores.

Visit 1:

Upon entering the study, patients are sensitized to squaric acid dibutyl ester (SADBE) by dipping a cotton-tipped swab in a 2% solution of SADBE in DMSO and swabbing a 1 cm$^2$ area on the forearm. Participants are told then to wait at least 2 weeks for their first treatment.

Throughout the study, the participants are asked to maintain a subject diary, in which they record each day any symptoms they experience, including fever, swelling, pain, redness, itching, burning, the size of any lesions, and any medications taken.

Visit 2:

After the 2-week period to allow development of sensitivity to SADBE, upon the beginning of his or her next outbreak (within 72 hours of the first signs of an outbreak), each participant is swabbed at the site of the herpes labialis lesion with a 0.5% solution of SADBE in DMSO.

Visit 3:

Upon the next distinct outbreak at least 2 weeks after the previous treatment at visit 2, study diaries are collected. If the diary reflects redness, blistering, or burning greater than 0.5 cm beyond the clinical lesion with the previous SADBE treatment, the dosage of SADBE is decreased to 0.1%. If the diary reflects no redness or inflammation attributable to SADBE treatment, dosage is increased to 2%. Otherwise, dosage is maintained at 0.5%. Participants are swabbed at the site of the herpes labialis lesion with the SADBE solution.

If the hypersensitivity reaction produced by SADBE is excessive, patients are treated with a topical steroidal anti-inflammatory cream. When a patient requests, outbreaks are treated with oral valacyclovir until the outbreak resolves.

For at least 6 months after visit 2, patients maintain their diaries. Every two months the diaries are collected.

At visit 1, before applying SADBE, a blood sample is collected from each patient for use in a peripheral blood mononuclear cell (PBMC) proliferation assay to test immune response to herpes virus.

Two months after visit 2 (the first treatment application of SADBE to an HSV lesion) if the patient has not experienced a recurrence outbreak after visit 2, or one month after visit 3 (the treatment application of SADBE to a lesion of a second outbreak), a blood sample is collected from the patient. The first, pretreatment, blood sample and the second, posttreatment, blood sample are used to conduct PBMC proliferation assays to test immune response to herpes virus before and after treatment.

PBMC Proliferation Assay

Venous blood is collected in heparinized test tubes for mononuclear cell isolation prior to treatment and after treatment at the times described above. Sample specimens are immediately transferred to the laboratory for processing.

Venous blood (15 ml) is transferred to a 50 ml centrifuge tube, diluted to a total volume of 30 ml with saline or PBS, underlayed with Fico/Lite-LymphoH™ (Atlanta Biologicals) and centrifuged for 20 minutes at 2100 rpm in an Eppendorf Model 5804R centrifuge. Interface cells are collected and washed 2× with saline/PBS, centrifuged and resuspended in saline/PBS. Cell counts are performed using a Beckman Coulter Z1 particle counter and the cells resuspended in freezing media (RPMI/20% human AB serum) and stored at −70° C. Pre- and post-treatment peripheral blood mononuclear cells from each patient are stored for proliferation assays.

KOS HSV-1 virus (American Type Culture Collection) is grown in culture in VERO cells and collected. Virus is filtered through a 45 µm filter attached to a 3 ml syringe, into sterile cryovials. The titer of the virus stock is determined. Virus is then heat inactivated, and stored at −20° C. for use to stimulate PMBC in the proliferation assays.

Peripheral blood mononuclear cells are thawed, washed 2× in saline/PBS and resuspended at 5×10$^5$ cell/ml in RPMI/ 10% human AB serum. Cells are plated at 200 µl/well. Heat inactivated KOS HSV-1 particles (2×10$^5$ pfu per well) are added to the experimental wells. Concanavalin A (5 µg/ml) is added to other wells as a positive control. Negative control wells have no additions. Plates are incubated at 37° C., 5% $CO_2$ for 5 days and then assayed for proliferation with Cell Counting Kit 8, a tetrazolium dye assay (Dojindo Molecular Technologies, Gaithersburg, Md.).

Results are calculated by averaging optical density of the wells in each of the groups. A stimulation index is calculated to reflect the proliferation in the wells stimulated by killed HSV as compared to the positive and negative controls. The average optical absorbance of the positive controls is set as a stimulation index (SI) value of 100 and the average absorbance of the negative controls as a SI value of 0.

Results:

After the sensitizing dose of SADBE and then two treatments on the lesions in the next two outbreaks, patients experience fewer outbreaks than before treatment, and the outbreaks they experience last for less time.

The stimulation index of PBMC from patients in a proliferation assay with stimulation by killed KOS HSV-1 particles is increased after treatment as compared to before the treatment.

All patents, patent applications, and other publications cited are incorporated by reference.

What is claimed is:

1. A pharmaceutical composition consisting essentially of squaric acid dibutylester (SADBE) dissolved in dimethyl-sulfoxide (DMSO), wherein the SADBE is at a concentration in the composition of 0.05% to about 2% (wt./vol).

2. The pharmaceutical composition of claim 1 consisting of SADBE dissolved in DMSO.

3. The pharmaceutical composition of claim 2 wherein the SADBE is at a concentration in the composition of 0.05% (wt./vol.) to 2.0% (wt./vol).

4. The pharmaceutical composition of claim 1 wherein the SADBE is at a concentration in the composition of 0.05% (wt./vol.) to 2.0% (wt./vol).

5. The pharmaceutical composition of claim 1 wherein the composition is in unit dosage form consisting of a volume of at least 2 microliters to no more than 40 microliters.

6. The pharmaceutical composition of claim 2 wherein the composition is in unit dosage form consisting of a volume of at least 2 microliters to no more than 40 microliters.

7. The pharmaceutical composition of claim 3 wherein the composition is in unit dosage form consisting of a volume of at least 2 microliters to no more than 40 microliters.

8. The pharmaceutical composition of claim 4 wherein the composition is in unit dosage form consisting of a volume of at least 2 microliters to no more than 40 microliters.

* * * * *